United States Patent
Tovey

(10) Patent No.: US 6,660,258 B1
(45) Date of Patent: Dec. 9, 2003

(54) OROMUCOSAL CYTOKINE COMPOSITIONS AND USES THEREOF

(75) Inventor: Michael Gerard Tovey, Paris (FR)

(73) Assignee: Pharma Pacific Pty Ltd, Laverton North (AU)

( * ) Notice: Subject to any disclaimer, the term of this patent is extended or adjusted under 35 U.S.C. 154(b) by 0 days.

(21) Appl. No.: 09/169,844

(22) Filed: Oct. 9, 1998

Related U.S. Application Data

(63) Continuation-in-part of application No. 08/853,870, filed on May 9, 1997, now Pat. No. 6,207,145, and a continuation-in-part of application No. 08/853,293, filed on May 9, 1997, now Pat. No. 5,997,858, and a continuation-in-part of application No. 08/853,292, filed on May 9, 1997.

(51) Int. Cl.$^7$ .................. A61K 45/00; A61K 39/00; A61K 38/00; C07K 17/08

(52) U.S. Cl. .................. 424/85.2; 424/198.1; 519/2; 530/351

(58) Field of Search .................. 519/2; 424/85.2, 424/198.1; 530/351

(56) References Cited

U.S. PATENT DOCUMENTS

| | | | |
|---|---|---|---|
| 4,605,555 A | 8/1986 | Sato et al. | 424/85 |
| 4,820,514 A | 4/1989 | Cummins | 424/85.4 |
| 5,017,371 A | 5/1991 | Cummins | 424/85.6 |
| 5,019,382 A | 5/1991 | Cummins, Jr. | 424/85.4 |
| 5,188,828 A | 2/1993 | Goldberg et al. | 424/85.2 |
| 5,215,741 A | 6/1993 | Young et al. | 424/85.7 |
| 5,286,748 A | 2/1994 | Eby, III | 514/494 |
| 5,449,515 A | 9/1995 | Hamilton et al. | 424/85.2 |
| 5,601,814 A | 2/1997 | Barton et al. | 424/85.2 |
| 5,654,000 A * | 8/1997 | Poli et al. | 424/450 |
| 5,665,345 A * | 9/1997 | Yarchoan et al. | 424/85.2 |
| 5,679,339 A * | 10/1997 | Keith et al. | 424/85.2 |
| 5,958,671 A * | 9/1999 | Glimcher et al. | |
| 6,045,788 A * | 4/2000 | Smith | 424/85.2 |
| 6,509,313 B1 * | 1/2003 | Smith | 514/2 |

FOREIGN PATENT DOCUMENTS

| | | |
|---|---|---|
| CA | 1320905 | 8/1993 |
| EP | 0 396 903 | 3/1990 |
| EP | 0 578 823 A1 | 1/1994 |
| JP | 3236328 A | 10/1991 |
| JP | 5124957 A | 5/1993 |
| JP | 5148155 A | 6/1993 |
| JP | 5213767 A | 8/1993 |
| WO | WO 82/00588 | 4/1982 |
| WO | WO 91/07186 | 5/1991 |
| WO | WO 91/16917 | 11/1991 |
| WO | WO 92/08493 | 5/1992 |
| WO | WO 92/10207 | 6/1992 |
| WO | WO 92/11030 | 7/1992 |
| WO | WO 96/10395 | 4/1996 |
| WO | WO 96/25171 | 8/1996 |
| WO | WO 97/25862 | 7/1997 |
| ZA | 94/1654 | 3/1994 |

OTHER PUBLICATIONS

Xiao et al, "Suppression of acute and protracted–relapsing experimental allergic encephalomyelitis by nasal administration of low–dose Il–10 in rats", *J Neuroimmunology* 84:230–237 (1998).

Hayden, Frederick G., "Intranasal Interferon α2 for Prevention of Rhinovirus Infection and Illness", The Journal of Infectious Diseases, vol. 148, No. 3 Sep. 1983. pp. 543–550.

Boguniewicz et al., "The Effect of Nebulized Recombinant Interferon–γ in Asthmatic Airways", *J. Allergy Clin. Immunol.* 95:133–135 (1995).

Brod et al., "Oral Administration of IFN–α is Superior to Subcutaneous Administration of IFN–α in the Suppression of Chronic . . . ", *Journal of Autoimmunity* 9:11–20 (1996).

Douglas et al., "Prophylactic Efficacy of Intranasal Alpha$_2$–Interferon Against Rhinovirus Infections in the Family Setting" 314: 65–70 (1986).

Hayden et al., "Intranasal Interferon α2 for Prevention of Rhinovirus Infection and Illness", *Journal of Infectious Diseases* 148:543–550 (1983).

Hayden et al., "Human Tolerance and Histopathologic Effects of Long Term Administration of Intranasal Interferon–α2", *Journal of Infectious Diseases* 148:914–921 (1983).

Hayden et al., "Prevention of Natural colds by Contact Prophylaxis with Intranasal Alpha$_2$–Interferon", *New England Journal Of Medicine* 314:71–75 (1986).

Hayden et al., "Human Nasal Mucosal Responses to Topically Applied Recombinant Leukocyte A Interferon", *Journal of Infectious Diseases* 156:64–72 (1987).

Iida et al., "Protective Activity of Recombinant Cytokines Against Sendai Virus and Herpes Simplex Virus (HSV) infections in mice", *Vaccine* 7:229–233 (1989).

Kaido, T.J., "Intranasal administration of IFN–α/β inhibits the development of visceral tumor metastases," *Journal of Interferon and Cytokine Research*, 17:31–36 (1997).

Machida et al., "Absorption of recombinant human granulocyte colony–stimulating factor (rhG–CSF) from rat nasal mucosa," *Pharmaceutical Research*, 10:1372–1377 (1993).

Matsuzawa et al., "Protective Effect of Mucosal Administration of Recombinant Human Macrophage Colony–Stimulating Factor . . . ", *Vaccine* 15:85–89 (1997).

Oehling et al., "Suppresion of the Immune System by Oral Glucocorticoid Therapy in Bronchial Asthma", *Allergy* 52:144–154.

Samo et al., "Efficacy and Tolerance of Intranasally Applied Recombinant Leukocyte A Interferon in Normal Volunteers", *Journal of Infectious Diseases* 148:535–542 (1983).

(List continued on next page.)

Primary Examiner—Yvonne Eyler
Assistant Examiner—J. Andres
(74) Attorney, Agent, or Firm—Browdy and Neimark, P.L.L.C.

(57) ABSTRACT

Pharmaceutical compositions for oromucosal; contact to stimulate host defense mechanisms in a mammal, having an effective amount of Th1 or Th2 stimulating cytokine, and methods of treatment with such compositions are provided.

66 Claims, No Drawings

OTHER PUBLICATIONS

Samo et al., "Intranasally Applied Recombinant Leukocyte A Interferon in Normal Volunteers. II.", *Journal of Infectious Diseases* 150:181–188 (1984).

Soos et al., Oral Feeding of Inteferon τ Can Prevent the Acute and Chronic Relapsing Forms of Experimental Allergic Encephalomyelitis, *Journal of Neuroimmunology* 75:43–50 (1997).

Takada et al., "Pharmacological Activity of Tablets Containing Recombinant Human Granulocyte . . . ", *International Journal of Pharmaceutics* 101:89–96 (1994).

Vriesendorp et al., "Oral Administration of Type I Inteferon Modulates the Course of Experimental Allergic Neuritis", *Autoimmunity* 24:157–165 (1996).

Watanabe et al., "Absorption and Blood Leukocyte Dynamics of Recombinant Human Granulocyte Colony–Stimulating Factor . . . ", *International Journal of Pharmaceutics* 110:93–97 (1994).

Yoshino, S., "The preventive effect of oral administration of type I interferon on collagen–induced arthritis in rats," *Experimental and Molecular Pathology*, 62:123–130 (1995).

Zielinska et al., "Comparison of the Long–Term Effects of Treatment with Oral and Parenteral . . . ", *Archivum Immunologiae et Therapiae Experimentalis* 44:359–366 (1996).

Moore et al., "Inflammatory Markers in Bronchoalveolar Lavage Fluid of Standardbred Racehorses with Inflammatory . . . ", *Equine Veterinary Journal* 29:142–147 (1997).

Ianaro, et al., "Expression of TGF–β in attenuated *Salmonella typhimurium*: oral administration leads to the reduction of inflammation, IL–2 and IFN–γ, but enhancement of IL–10, in carrageenin–induced oedema in mice," *Immunology*, 84:8–15 (1995).

Koren et al., "Modulation of peripheral leukocyte counts and bone marrow function in mice by oral administration of interleukin–2," *Journal of Interferon Research*, 14:343–347 (1994).

Marinaro et al., "Interleukin–12 alters helper T–cell subsets and antibody profiles induced by the mucosal adjuvant cholera toxin," *Annals New York Academy of Sciences*, 361–365 (Oct. 31, 1996).

Marinaro et al., "Oral but not parenteral interleukin (IL)–12 redirects T helper 2 (Th2)–type responses to an oral vaccine without latering mucosal IgA responses," *J. Exp. Med.*, 185:415–427 (1997).

Marinaro et al., "Intranasal IL–12 delivery enhances Th2–type while oral IL–12 redirects Th2–to Th1–type responses," *J. Immunol.*, 99:534 (1997).

Sur et al., "Immunomodulatory effects of IL–12 on allergic lung inflammation depend on timing of doses," *J. Immunol.*, 157:4173–4180 (1996).

* cited by examiner ns. OROMUCOSAL CYTOKINE COMPOSITIONS
AND USES THEREOF

CROSS REFERENCE TO RELATED APPLICATIONS

This application is a continuation-in-part of U.S. Ser. No. 08/853,870, filed May 9, 1997, now U.S. Pat. No. 6,207,145, 08/853,293, filed May 9, 1997, now U.S. Pat. No. 5,997,858, and 08/853,292, filed May 9, 1997, the disclosures of which are incorporated by reference herein.

FIELD OF THE INVENTION

This invention relates to methods of stimulation of host defense mechanisms in a mammal by administration of Th1 or Th2 specific cytokines via the oromucosa, as well as to compositions for oromucosal delivery of Th1 or Th2 specific cytokines. In particular, the invention is applicable to methods of treatment of autoimmune, allergic, inflammatory, intracellular bacterial, neoplastic, neurological, parasitic, and viral diseases.

BACKGROUND OF THE INVENTION

Interleukins (ILs) are a diverse class of secreted peptides and proteins whose principal function is the mediation of local interactions among cells. Most information regarding ILs comes from work with leukocytes, especially lymphocytes.

It is now generally accepted that CD4 T cells can be divided into two functionally distinct subsets, T helper 1 (Th1) and T helper 2 (Th2) cells, characterized by the pattern of cytokines which they produce. Thus, mouse Th1 cells produce interferon γ (IFN-γ), tumor necrosis factor β (TNF β), and interleukin 2 (IL-2), whereas mouse Th2 cells produce IL-4, IL-5, IL-6, IL-9, IL-10, and IL-13. Human Th1 and Th2 cells have similar patterns of cytokine secretion, although the synthesis of IL-2, IL-6, IL-10, and IL-13 is not as tightly restricted to a single subset as in the mouse. Several other cytokines are secreted by both Th1 and Th2 cells, including IL-3, TNF α, granulocyte-macrophage colony-stimulating factor (GM-CSF), Met-enkephalin, and certain chemokines-(CK). Other novel cytokines, such as IL-18 (Yoshimoto et al. 1997, Proc. Natl. Acad. Sci. USA, 94, 3948–3953), originally designated interferon gamma inducing factor (IGIF), which potentiates Th1 responses continue to be described, and it is highly probable that other novel cytokines which influence either a Th1 or Th2 response, will be discovered in the future.

Th1 and Th2 patterns of cytokine secretion correspond to activated effector phenotypes generated during an immune response. They do not exist among naive T cells. Thus, when first stimulated by antigen on antigen-presenting cells (APC), naive CD4+ T cells initially produce only IL-2, and then differentiate into phenotypes that secrete other cytokines. A third class of CD4+ T. cells, designated Th0 cells, has been identified, which consists of partially differentiated effector cells which express both the Th1 and Th2 patterns of cytokine expression and may represent a transient stage along the differentiation pathway into Th1 and Th2 cells. A fourth class of CD4+ T cells termed Th3 cells, producing high levels of transforming growth factor P (TGFP), has also been recognized.

Th1 and Th2 cells not only produce different sets of cytokines, resulting in distinct functional properties, but also preferentially express certain activation markers. Thus, human Th1 cells preferentially express lymphocyte activation gene 3 (LAG-3), a member of the immunoglobulin superfamily, while human Th2 cells preferentially express CD 30, a member of the TNF receptor family. LAG-3 expression is enhanced by IFN γ and inhibited by IL-4, while CD 30 expression is dependent upon the presence of IL-4. Th1 cells also express E-selectin, p-selectin ligands and the βchain of the IL-12 receptor, which are not expressed by Th2 cells.

CD8+ T cell cytotoxic (Tc) cell subsets can also be distinguished on the basis of the cytokines they produce. Thus, Tc1 cells secrete IL-12 and IFN γ and cells with a Tc2 profile secrete IL-4 and IL-5 and are found in certain pathological conditions, such as lepromatous leprosy and HIV infected individuals with high IgE levels.

The functions of Th1 and Th2 cells correlate well with their distinctive cytokines. Thus Th1 cells are involved in cell mediated immune responses (macrophage activation, antibody-dependent cell cytotoxicity and delayed type hypersensitivity) and resistance to virus infection, and several Th1 cytokines activate cytotoxic and inflammatory reactions. Th2 cytokines potentiate antibody production, particularly IgE responses, and also enhance mucosal immunity through production of growth and differentiation factors for mast cells and eosinophils. Accordingly, Th2 cells are associated with antibody production, allergic reactions, and susceptibility to virus infection.

Th1 and Th2 cytokines are mutually inhibitory for the differentiation and effector functions of the reciprocal phenotype. Thus, IL-12 and IFN γ selectively inhibit the proliferation of Th2 cells and IL-4 and IL-10 inhibit Th1 development. In many cases the use of cytokines or anticytokines can reverse host resistance or susceptibility to infection. See the Th1–Th2 Paradigm, Sergio Romagani, Immunology Today, June 1997, 18:6 (263–266).

Interleukin-2 (IL-2) is a biological response modifier which activates cytolytic T-cells and natural killer cells (see Kuziel, W. A. and Gree, W. C. (1991), Interleukin-2, in The Cytokine Handbook, A. Thompson (Ed.), San Diego, Calif., Academic Press, pages 83–102). Therefore, IL-2 has been examined for its therapeutic potential against malignancies, immunodeficiencies and chronic infections.

Basically, IL-2 regulates the proliferation and differentiation of T-lymphocytes and other lymphoid cells, by binding to a high affinity cell surface receptor composed of three polypeptide chains: alpha, beta and gamma (Waldmann, T. A., 1993, Immunol. Today, 14:264). Data presented by Vasily Gelfanov et al. (Proceedings of the Keystone Symposium on Mucosal Immunity, 1997, S1124:12) show that intestinal intra-epithelial lymphocytes, which are known to differ in a number of important respects from T-cells of the central immune system, respond preferentially to a recently identified T-cell growth factor, interleukin 15 (IL-15), rather than to the classical T-cell growth factor, IL-2.

IL-15 interacts with a heterotrimeric cell surface receptor that consists of the beta and gamma subunits of the IL-2 receptor as well as a specific high-affinity IL-15 binding subunit designated IL-15R alpha. Since both the beta and gamma subunits of the IL-2 receptor are required for signalling by either IL-2 or IL-15, it is not surprising that these two cytokines have been reported to share a number of common biologic activities (Kennedy, M. K. and Park L. S., 1996, J. Clin. Immunol., 16:134–143).

In common with interferon alpha, IL-12 is one of the principal regulators of natural killer (NK) cell activity, which plays an important role in host defense against neoplastic cells (Kobayashi, M., 1989, J. Exptl. Med., 170:827). IL-12, which is produced principally by macrophages, also induces the release of interferon gamma by activated T-cells and NK cells, and synergizes with IL-2 to generate lymphokine-activated killer (LAK) cells (Aragane et al., 1994, J. Immunol., 153:5366–5372). IL-12 together with IL-2 and interferon gamma plays a pivotal role in the development of T helper type 1 (Th1) effector cells. A Th1 response is often associated with resistance to infection and has been shown to play a decisive role in the antiviral action of interferon alpha 2 in patients infected with human papillomavirus (Arany, I. and Tyring, K., 1996, J. Interferon and Cytokine Res., 16:453–460).

The antitumor activity of systemically administered IL-2 is thought to be mediated principally by LAK cells (Natuk et al., 1989, J. Virol., 63:4969–4971). The antiviral activity of systemically administered IL-2 is thought to be mediated principally by macrophage mediated antibody-dependent cellular cytotoxicity (ADCC), which involves the induction of interferon gamma in helper T-cells (Kohe et al., J. Inf. Dis., 159:239–247), and through LAK cells (Natuk et al., 1989, J. Virol.; 63:4969–4971).

Interleukins are generally administered parenierally. However, parenteral administration of IL-2 is associated with a number of severe side-effects, such as hematological toxicity and renal dysfunction (see Haworth, C., and Feldmann; M., 1991, Applications of cytokines in human immunotherapy in The Cytokine Handbook, A. Thompson (Ed.), San Diego, Calif.: Academic Press, pages 301–324). Similar toxic effects have been observed for a number of other interleukins.

Systemically administered recombinant human IL-2 has also been used extensively for the treatment of a number of neoplastic diseases, including renal cell carcinoma (Rozenberg et al., 1989, Ann. Surg., 210:474) and malignant melanoma (Rozenberg et al., 1987, New Engl. J. Med., 316:889), and to a lesser extent for the treatment of certain virus diseases including chronic hepatitis B (Kakumu, et al., 1988, Hepatology, 8:487–492). In all these studies considerable toxicity has been encountered, including fever, chills, anorexia and fatigue (Kakumu et al., 1988, Hepatology, 8:487–492).

A series of patents and patent publications mention in general terms, inter alia, the possibility of oral administration of various interleukins. For example, WO 91/16917 discloses IL-1 for the treatment of gastric ulcers. and obesity; WO 92/11030 discloses IL-4 for enhancing the immune response to inumunogens in vaccines; U.S. Pat. No. 5,601, 814 discloses IL-6 for treating toxic shock; U.S. Pat. No. 5,188,828 discloses IL-6 for enhancing endogenous erythropoietin levels; and WO 96/25171 discloses IL-12 for inhibiting angiogenesis. However, these general disclosures do not comprehend actual oral absorption of the active ingredient, nor do any of the examples include reports of oral absorption or of protein activity after oral delivery. For example, while U.S. Pat. No. 5,449,515 discloses in general terms oral delivery of IL-4, it also discloses that IL-4 if incorporated in an oral dosage form may be coated by, or administered with, a material to prevent its inactivation and discusses various materials to be used to avoid inactivation. The measures proposed include enzyme inhibitors and the incorporation of the interleukin in liposomes (see Column 3, lines 7–22). It is clear that administration by mouth for delivery to the small intestine is actually contemplated by these references.

Koren S. and Fleischmann W. R. Jr., Journal of Interferon Research, 14(6):343–7, December 1994, described the modulation of peripheral leukocyte counts and bone marrow function in pathogen-free mice by oral administration of rhIL-2 and ascertained levels of suppression of white blood cell numbers similar to those achieved with a subcutaneous dose. They concluded that orally administered IL-2 can exert systemic effects and speculated that the oral administration of IL-2 may have therapeutic potential. Marinaro, M., Boyaka, P. N., Finkelman, F. D., Kiyono, H., Jackson, R. J., Jirillo, E., and McGhee, J. R., J. Exp. Med., Feb 3 1997, 185 (3) pages 415–27 ascertained that intragastric but not parenteral administration of recombinant murine IL-12 (rmIL-12) redirects T helper 2 (Th2)-type responses to an oral vaccine without altering intestinal mucosal IgA responses. The authors concluded that IL-12 can be administered by the "oral" route for regulation of systemic response to an oral vaccine and suggested that oral IL-12 formulated for delivery to the Peyer's patches of the small intestine can also exert immunomodulaiory effects at the mucosal level.

Marinaro, M., Boyaka, P. N., Jackson, R. J., Finkelman, F. D., Kiyono, H., McGhee, J. R., J. Allergy Clin. Immunol., 99, No. 1, Pt.2, S34, 1997 investigated intranasal versus oral delivery of IL-12 complexed to liposomes. They found that intranasal IL-12 delivery exacerbates Th2-type responses, while oral IL-12 redirects Th2- to Th1-type responses. This shows that delivering IL-12 by two different mucosal routes resulted in opposite types of mucosal and systemic immune responses to an oral vaccine. Furthermore, the clinical use of IL-12 in patients with renal cancer is associated with substantial toxicity (Cohen J., Science, 1995, 270, 908).

However, it is clear that in all of these patent and literature publications "oral delivery" means administration by mouth for delivery to the small intestine, where the IL is actually absorbed.

We have now surprisingly found that administration of Th1 specific cytokines to the oromucosa has a dramatic effect in prolonging the survival of mice following challenge with viruses and tumors which are normally rapidly lethal.

SUMMARY OF THE INVENTION

This invention provides a method for stimulating host defense mechanisms in a mammal via the oromucosal administration of a Th1 or Th2 specific cytokine preferably at doses which induce a host-defense mechanism stimulating effect, compositions for the oromucosal delivery of the cytokines and methods of treating disease states with the cytokines.

The invention also provides a method of stimulating an immune response in a mammal comprising the step of administering to the mammal an immunostimulating amount of a Th1 or Th2 specific cytokine via oromucosal contact.

Preferably the Th1 cytokine is selected from the group consisting of interferon-α, interferon-β, interferon-ω, interferon-γ, IL-2, IL-12, IL-15, IL-18, GM-CSF; and tumor necrosis factor-beta (lymphotoxin). Preferably the Th2 cytokine is selected from the group consisting of IL-4, IL-5, Il-10, and IL-13. Preferably the cytokine is produced by recombinant DNA technology.

The methods and compositions of the invention are applicable to the treatment of both humans and non-human mammals, including companion animals such as cats and dogs, and domestic animals such as horses, cattle, and sheep.

The method of the invention also permits administration of an amount of a Th1 or Th2 specific cytokine which is in excess of a dose of the same cytokine as that which induces a pathological response when administered parenterally.

Alternatively, the invention provides a method for increasing the therapeutic index of Th1 or Th2 cytokine by administering the cytokine oromucosally.

DETAILED DESCRIPTION OF THE INVENTION

The invention will now be described in detail by way of reference only using the following definitions and examples. All patents and publications referred to herein are expressly incorporated by reference.

The term "oromucosa" refers to the mucosa lining the oral and/or nasopharyngeal cavities. For the purposes of the animal experiments described in this specification, the expressions "oromucosal", "oropharyngeal", "intranasal/oral", "intranasal plus oral", and "in/or" with reference to the route of administration of cytokine are synonymous, and are to be taken to mean administration of the cytokine preparation deep into the nasal or oral cavity so that cytokine is rapidly distributed into the mouth and throat of the recipient mammal, so as to make contact with the mucosal lining of this cavity. While it is the site of absorption, not the method of administration, which is critical, it is not necessary that the cytokine contact the whole of the mucosal lining of the nasal, oral, and pharyngeal cavities.

When used herein without further qualification, the term "cytokine" refers to a Th1 or Th2 specific cytokine, i.e. a cytokine which stimulates the activity of Th1 or Th2 cells.

As used herein, "interleukin" refers to a cytokine protein produced by lymphocytes, including but not limited to those commonly designated as IL-2, IL-3, IL-4, IL-5, IL-10, IL-12, IL-1 3, IL-1 5, IL-18 and mixtures thereof. The interleukin may be derived from natural sources, but is preferably a recombinant product. For the purposes of the invention, the term "cytokine" also includes polypeptides or their fragments which have cytokine activity, and chimeric or mutant forms of cytokine in which sequence modifications have been introduced, for example to enhance stability, without affecting the nature of their biological activity. Other modifications such as pegylated forms and fusion proteins with immunoglobulins or other proteins are also within the scope of the invention.

The oromucosal administration may involve administering an effective dose of cytokine in a single dose, or the effective dose may be administered in a plurality of smaller doses over a period of time sufficient to elicit immunostimulation equivalent to that of a single dose. Likewise, the dose of cytokine may be administered continuously over a period of time sufficient to induce an effect equivalent to that of a single dose.

The invention provides a method for treating a condition selected from the group consisting of intracellular bacterial infections, neurological diseases, allergic conditions, inflammatory conditions, neoplastic diseases, parasitic infections, and viral infections, comprising the step of administering to the mammal an effective amount of a Th1 specific cytokine via oromucosal contact.

Further, the invention provides a method for treating autoimmune diseases including but not limited to rheumatoid arthritis, Type I diabetes, lupus erythematosus, multiple sclerosis, and psoriasis by the oromucosal administration of a Th2 cytokine.

Inflammatory conditions such as ulcerative colitis and Crohn's disease, intracellular bacterial infections including Listeria, mycobacterial infections such as leprosy and tuberculosis, neurological diseases including multiple sclerosis and amyotrophic lateral sclerosis, parasitic diseases such as malaria, schistosomiasis and leishmaniasis, and CMV infections and allergic conditions including asthma and atopic dermatitis can be treated by oromucosal administration of a cytokine.

The invention also provides a method for treating neoplastic conditions such as multiple myeloma, hairy cell leukemia, chronic myelogenous leukemia, low grade lymphoma, cutaneous T-cell lymphoma, carcinoid tumors, cervical cancer, sarcomas including Kaposi's sarcoma, carcinomas including renal cell carcinoma, hepatocellular carcinoma, nasopharyngeal carcinoma, hematological malignancies, colorectal cancer, glioblastoma, laryngeal papillomas, lung cancer, colon cancer, malignant melanoma, and brain tumors including malignant brain tumors.

While the method of the invention may be used without concurrent treatment with other agents, it is contemplated that this embodiment of the invention will be particularly useful in the following settings:

a) as adjuvant therapy, subsequent to surgery, chemotherapy, or radiotherapy (x-ray, UV) given by standard protocols;

b) for treatment of cytokine-sensitive neoplasias, the method of the invention is utilized either alone or in conjunction with conventional chemotherapy or radiotherapy; and c) for treatment of cytokine-resistant neoplasias, the method of the invention is utilized either alone or most preferably in conjunction with conventional chemotherapy or radiotherapy.

In a third embodiment the disease to be treated is a viral infection. The viral infection may be an acute or fulminant infection, such as rhinovirus, influenza, Herpes zoster, dengue fever, or viral encephalitis including but not limited to measles virus encephalitis, Murray Valley encephalitis, Japanese B encephalitis, tick-borne encephalitis and Herpes encephalitis; haemorrhagic fevers such as Ebola virus, Marburg virus, Lassa fever; Hanta virus infections, and other viral infections thought to be transmitted from animals to humans, such as equine morbillivirus. In many of these conditions, there is no treatment and/or vaccine presently available, and supportive treatments may be inadequate. Alternatively, the viral condition may be the result of chronic infection, such as hepatitis B, C, D, or other forms of viral hepatitis, or cytomegalovirus (CMV), human immunodeficiency virus (HIV), human papillomavirus (HPV), and herpes simplex I & II (HSV I & II).

Again the method and dosage form of the invention may be used in conjunction with other treatments. For example, for herpes virus infection acyclovir or ganciclovir may be used. For HIV infection azidothymidine (zidovudine) or one or more other HIV reverse transcriptase inhibitors, and/or HIV protease inhibitors may be used.

In a fourth embodiment, the disease to be treated is malaria, and again a cytokine is administered as described above. The causative organism of the malaria may be Plasmodium malariae, Plasmodium vivax, Plasmodium falciparum or Plasmodium ovale. It is particularly contemplated that the method of the invention will protect against progression of malaria to the cerebral form. Optionally, an anti-malarial drug, for example chloroquine, may also be used.

A further aspect of the invention is the use of a pharmaceutical composition for oromucosal stimulation of host defense mechanisms in a mammal which composition comprises a Th1 or Th2 stimulating cytokine and at least one pharmaceutically acceptable excipient useful for oromucosal delivery.

As mentioned above, in the present invention, the embodiments presented as preferred for the methods for stimulating host defense mechanisms are also the preferred embodiments for the uses of the Th1 or Th2 cytokines for preparing an oromucosal drug for stimulating host defense mechanisms in a mammal.

In another aspect, the invention provides a pharmaceutical composition for oromucosal administration comprising a therapeutically effective amount of at least one Th1 or Th2 specific cytokine, and a pharmaceutically acceptable carrier adapted, for oromucosal administration. The composition may be provided as a solution, tablet, lozenge, gel, syrup, nasal spray, nasal drops, inhalable formulation, paste, or controlled release oromucosal delivery system. Optionally, the composition may contain buffers, stabilizers, thickening agents, absorption and viscosity enhancers, and the like.

The method may be practiced either as the sole therapeutic approach, or as an adjunct to radiation therapy, chemotherapy, or treatment with one or more other agents, or with interferon-inducers or interleukin-inducers. In some circumstances more than one cytokine may be used, concomitantly or subsequently, to take advantage of alternative mechanisms of action.

Our results so far indicate that there are no significant toxic and, at worst, only minor side-effects of oromucosal administration of cytokines. Thus the method of the invention also permits administration of an amount of a Th1 or Th2 specific cytokine which is in excess of a dose of the same cytokine as that which induces a pathological response when administered parenterally. Alternatively, the invention provides a method for increasing the therapeutic index of a Th1 or Th2 specific cytokine by administering the cytokine oromucosally.

Oromucosal cytokines can be given at a dose lower than, equal to, or higher than, the parenteral dose level at which stimulation of the host defense mechanismn occurs. In a particularly preferred form of the invention the total dose is from about 0.01 $\mu$g/kg to about 150 $\mu$g/kg.

Optionally the cytokine may be administered with an inducer or potentiator of production, activation, or release of cytokines. The inducer may be administered together with the oromucosal cytokine or may be administered separately. Inducers of ILs are known; for example,bacterial liposaccharide stimulates release of a variety of ILs and other cytokines.

The methods, uses and compositions of the invention may optionally be used in conjunction with one or more other treatments for the specific condition, and the attending physician or veterinarian will readily be able to select such other treatment as may be appropriate in the circumstances.

The methods insofar as they relate to treatment of neoplastic conditions are directed at inducing and/or maintaining remission of disease. By "in conjunction with other treatment" is meant that the cytokine is administered before, during and/or after the surgery, radiotherapy or other chemotherapy. The most suitable protocol will depend on a variety of factors, as discussed below.

In particular, it is contemplated that the method of the invention will preferably be used in conjunction with at least one other treatment selected from the group consisting of chemotherapy using cytostatic drugs, one or more other cytokines which have anti-cancer activity, but which have a different mechanism of action from that of the oromucosal cytokine, anti-angiogenic agents, and agents which potentiate the activity of specific cytokines. Preferably the second cytokine is interferon $\alpha$, interferon $\beta$, interferon $\gamma$, interferon $\omega$ or consensus interferon; preferably the angiogenesis inhibitor is AGM-1470 [(Chloroacetyl)-carbamic acid (3R-(3 $\alpha$, 4$\alpha$ (2R*, 3R*), 5 $\beta$, 6$\beta$))-5-methoxy- 4-(2-methyl-3-(3-methoxy-2-butenyl) oxiranyl)-1-oxaspiro(2.5)oct-6-yl ester].

Examples of cancer chemotherapeutic agents are antimetabolites such as 6-mercaptopurine, 5-fluorouracil, cytosine arabinoside and the metabolites and derivatives of these agents. Other cancer chemotherapeutic agents are antifolates such as methotrexate or agents derived from natural products, for example, derived from vinca alkaloids, such as vinblastine, vincristine and colchicine; adriamycin, daunorubicin, doxorubicin, teniposide or etoposide. Such cancer chemotherapeutic agents also include platinum anticancer drugs, such as cisplatin and carboplatin. In addition, the agents of the present invention can be administered with cyclophosphamide, busulfone, procarbazine, dacarbazine, carmustine, lomustine, mechlorethamine, chlorambucil, hydroxyurea, nitroso urea and its derivatives, melphalan, mitotone, taxol, $\alpha$-difluoromethylornithine, and spirogermanium. Most commonly multidrug resistance is observed with the vinca alkaloids, the anthracyclines daunorubicin, doxorubicin and adriamycin; and etoposide and teniposide; less frequently with antimetabolites and the other chemotherapeutic agents.

Preferred cytostatic drugs to be administered in conjunction with the cytokine include but are not limited to cyclophosphamide, cisplatin, carboplatin, carmustine, methotrexate, adriamycin, $\alpha$-difluoromethyl-ornithine, and 5-fluorouracil.

In the preparation of the pharmaceutical compositions of this invention, a variety of vehicles and excipients for the cytokine may be used, as will be apparent to the skilled artisan. Representative formulation technology is taught in, inter alia, Remington: The Science and Practice of Pharmacy, 19th ed., Mack Publishing Co., Easton, Pa., 1995, and its predecessor editions. The cytokine formulation may comprise stability enhancers, such as glycine or alanine, as described in U.S. Pat. No. 4,496,537, and/or one or more carriers, such as a carrier protein. For example, for treatment of humans, pharmaceutical grade human serum albumin, optionally together with phosphate-buffered saline as diluent, is commonly used. Where the excipient for the cytokine is human serum albumin, the human serum albumin may be derived from human serum, or may be of recombinant origin.

The cytokine may be administered by means which provide contact of the cytokine with the oromucosal cavity of the recipient for a period of time sufficient to obtain the desired stimulation. Other mucosae may be similarly responsive. Thus it will be clearly understood that the invention is not limited to any particular type of formulation. The present specification describes administration of a cytokine deep into the oromucosal cavity; this may be achieved with liquids, solids, or aerosols, as well as nasal drops or sprays. Thus the invention includes, but is not limited to, liquid, spray, syrup, lozenges, buccal tablets, and nebuliser formulations. A person skilled in the art will recognize that for aerosol or nebuliser formulations the particle size of the preparation may be important, and will be aware of suitable methods by which particle size may be modified. Micronised formulations are specifically contemplated.

In one aspect, the cytokine is administered in a single dose. Alternatively, the cytokine is administered in a plurality of lower doses, distributed over time, so that the net effect is equivalent to the administration of the single higher dose. One approach to this delivery mode is via the provision of a sustained or controlled release device adhered to or implanted in the oromucosal cavity and designed to release cytokine over time in an amount equivalent to a single high dose.

One formulation of a cytokine for oromucosal use is the following (all % are w/w):

Tablet: Dextrose BP 45%; gelatin BP 30%; wheat starch BP 11%; carmellose sodium BP 5%; egg albumin BPC 4%; leucine USP 3%; propylene glycol BP 2%; and 1% cytokine. The tablet may be used as is and allowed to slowly dissolve in the mouth or may be dissolved in water and held in the mouth in contact with the oromucosa as needed.

A cytokine paste may be prepared, as described in U.S. Pat. No. 4,675,184, from glycerin 45%, sodium CMC 2%, citrate buffer (pH 4.5) 25%, distilled water to 100%, and 1% cytokine. The cytokine paste may be adhered to the buccal mucosa.

Likewise, a gargle or a syrup may be prepared by adding the desired amount of cytokine to a commercially available mouthwash or cough syrup formulation.

Within the specific dose ranges referred to above, the treatment in any individual case will depend upon the nature of the condition, the stage of disease, previous therapy, other continuing therapy, the general state of health of the mammal, the sensitivity of the subject to the cytokihne etc., and therefore will bc at the physician's or veterinarian's discretion, bearing in mind all these circumstances. The length of treatment will of course vary with the condition being treated, for example, treatment of a slow-growing cancer, such as prostate cancer, would be expected to involve a different course of treatment than treatment of a rapidly growing cancer, such as hepatocellular, carcinoma. Similarly, an acute infection such as that caused by Ebola virus would be expected to involve a different course of treatment than for a chronic condition, such as hepatitis.

The effective dose disclosed herein is one which may generate a pathological response in the mammal when administered parenterally, but is both effective and either non-toxic or less toxic when administered oro mucosally. A pathological response may be acute, chronic, or cumulative, and may be manifested by changes in blood chemistry, such as leukopenia, bone marrow depression, or other histological parameters. As used herein, a pathological response includes adverse side effects, such as fever, chills, anorexia, fatigue, malaise, or influenza-like symptoms, vascular reactions, such as phlebitis, and local inflammatory reactions at the site of injection. Such responses will vary considerably among the patient population in view of individual variations in sensitivity to cytokines.

For many patients, it is expected that oromucosal doses will exceed those known to be tolerated in existing approved parenteral protocols. In one embodiment, the total dose may be administered in multiple lower doses over time, or even may be delivered continuously or in a pulsatile manner from a controlled release device adhered to or implanted in the oromucosa.

In summary; the present invention is directed to

A method for stimulating host defense mechanisms in a mammal which method comprises administering to the mammal a stimulating amount of an Th1 or Th2 stimulating cytokine via oromucosal contact.

A said method for stimulating an immune response in a mammal which method comprises administering to the mammal a stimulating amount of a Th1 or Th2 stimulating cytokine via oromucosal contact.

A said method, wherein said amount is from about 0.01 $\mu$g to about 150 $\mu$g of cytokine per kg body weight.

A said method in which the effective amount of cytokine is administered in a single amount.

A said method in which the effective amount of cytokine is administered in a plurality of smaller amounts over a period of time sufficient to elicit stimulation equivalent to that of a single amount.

A method in which an stimulating amount of cytokine is administered continuously over a period of time sufficient to elicit stimulation equivalent to that of a single amount.

A method for stimulating host defense mechanisms in a mammal which method comprises administering to the mammal a stimulating amount of an Th1 stimulating cytokine via oromucosal contact.

A method for stimulating an immune response in a mammal which method comprises administering to the mammal a stimulating amount of a Th1 stimulating cytokine via oromucosal contact.

A said method wherein said amount is from about 0.01 $\mu$g to about 150 $\mu$g of cytokine per kg body weight.

A said method in which the effective amount of cytokine is administered in a single amount.

A said method in which the effective amount of cytokine is administered in a plurality of smaller amounts over a period of time sufficient to elicit stimulation equivalent to that of a single amount.

A said method in which a stimulating amount of cytokine is administered continuously over a period of time sufficient to elicit stimulation equivalent to that of a single amount.

A method for treating a neoplastic condition in a mammal which method comprises administering to the mammal an effective amount of a Th1 stimulating cytokine via oromucosal contact and a said method wherein the cytokine comprises interferon-ω, interferon-α, interferon-β, interferon-γ, interleukin-2, interleukin-12, interleukin-15, interleukin-18, tumor necrosis factor β, or granulocyte macrophage-colony stimulating factor (GM-CSF).

A method for treating a viral infection which method comprises administering to the mammal an effective amount of a Th1 stimulating cytokine via oromucosal contact and a said method wherein the cytokine comprises interferon-α, interferon-β, interferon-ω, interferon-γ, interleukin-2, interleukin-12, interleukin-15, interleukin-18, tumor necrosis factor-β, and granulocyte macrophage-colony stimulating factor (GM-CSF).

A method for treating an allergic disorder in a mammal which comprises administering to the mammal an effective amount of a Th1 cytokine via oromucosal contact and a said method wherein the cytokine is selected from the group consisting of interferon-α, interferon-β, interferon-ω, interferon-γ, interleukin-2, interleukin- 12, interleukin- 15, interleukin- 18, tumor necrosis factory-β, and GM-CSF.

A method for treating asthma which comprises administering to the mammal an effective amount of a Th1 cytokine via oromucosal contact and a said method wherein the cytokine is selected from the group consisting of interferon-α, interferon-β, interferon-ω, interferon-γ, interleukin-2, interleukin-12, interleukin-15, interleukin-18, tumor necrosis factor-β, and GM-CSF.

A method for treating atopic dermatitis which comprises administering to the mammal an effective amount of a Th1 cytokine via oromucosal contact and a said method wherein the cytokine is selected from the group consisting of interferon-α, interferon-β, interferon-ω, interferon-γ, interleukin-2, interleukin-12, interleukin-15, interleukin- 18, tumor necrosis factors, and GM-CSF.

A method for stimulating host defense mechanisms in a mammal which method comprises administering to the mammal a stimulating amount of an Th2 stimulating cytokine via oromucosal contact A method for stimulating an inmnune response in a mammal which method comprises administering to the mammal a stimulating amount of a Th2 stimulating cytokine via oromucosal contact.

A said method in which said amount is from about 0.01 μg to about 150 μg of cytokine per kg body weight.

A said method in which the effective amount of cytokine is administered in a single amount.

A said method, in which the effective amount of cytokine is administered in a plurality of smaller amounts over a period of time sufficient to elicit stimulation equivalent to that of a single amount.

A said method, in which an stimulating amount of cytokine is administered continuously over a period of time sufficient to elicit stimulation equivalent to that of a single amount.

A method for treating an autoimmune disease in a mammal which method comprises administering to the mammal an effective amount of a Th2 stimulating cytokine via oromucosal contact and said method wherein the cytokine is selected from the group consisting of interkeukin 4, interleukin 5, interleukin 10, and interleukin 13.

A said method wherein the cytokine comprises a recombinant cytokine.

The use of a Th1 or Th2 cytokine for preparing an oromucosal drug for stimulating host defense mechanisms in a mammal.

A pharmaceutical composition for oromucosal stimulation of host defense mechanisms in a mammal which composition comprises a Th1 or Th2 stimulating cytokine and at least one pharmaceutically acceptable excipient useful for oromucosal delivery.

A pharmaceutical composition in unit dosage form adapted for oromucosal administration comprisinig from about 0.01 μg to about 10 000 μg of a Th1 or Th2 stimulating cytokine and a pharmaceutically acceptable carrier and a said composition comprising from about 10μg to about 10 000 μg of cytokine.

A said composition comprising a Th1 cytokine.

A said composition comprising a Th2 cytokine.

I. Cytokine Formulations

Natural Murine Interferon-α/β

Murine interferon-α/β was prepared from cultures of C243-3 cells induced with Newcastle Disease Virus (NCV) and purified as described previously (Tovey et al, Proc. Soc. Exp. Biol. Med., 1974, 146:406–415). The preparation used in this study (lot no. T638) had a titer of $1 \times 10^6$ IU/ml and a specific activity of $5 \times 10^7$ IU/mg protein as assayed on mouse L929 cells challenged with Vesicular Stomatitis virus (VSV) (Tovey et al, Proc. Soc. Exp. Biol. Med., 1974, 146:406–415), and standardized against the international reference preparation of murine interferon α/β of the US National Institutes of Health (G-002-9004-5411).

Recombinant Murine Interleukin-2

Recombinant murine interleukin-2 (IL-2) was purchased from R & D Systems, Inc. (Minneapolis, Minn.). The preparation used in this study (Lot No. MX056111) was greater than 97% pure as determined by SDS-PAGE and had a ED50 of 0.1 to 0.4 ng/ml, measured in a cell proliferation assay using an IL-2 dependent murine cytotoxic T-cell line, CTLL-2 (Gearing, A. J. H. and C. B. Bird, 1987, Lymphokines and interferons, a practical approach, Clements, M. J., Morris, A. G. and A. J. H. Gearing, eds., IRL Press, p. 296).

Recombinant Murine Interleukin-4

Recombinant murine interleukin-4 (IL-4) was purchased from Protein Institute Inc. (Paris, France). The preparation used in this study (lot no. P 200M-04) was greater than 98% pure as determined by SDS-PAGE and N-terminal sequence analysis. The preparation had a ED50 of 2.0 ng/ml.

Recombinant Murine Interleukin-5

Recombinant murine interleukin-5 (IL-5) was purchased from R & D Systems Inc. The preparation used in this study (lot no. 405-ML-025) was greater than 97% pure as determined by SDS-PAGE, and had an ED50 of 0.04 to 0.15 ng/ml.

Recombinant Murine Interleukin-10

Recombinant murine interleukin-10 (IL-10) was purchased from Protein Institute Inc. The preparation used in this study (lot no. P 200M-10) was greater than 98% pure as determined by SDS-PAGE and N-terminal sequence analysis. The preparation had an ED50 of 2.0 ng/ml.

Recombinant Murine Interleukin-12

Recombinant murine interleukin-12 (IL-12) was purchased from R & D Systems, Inc. The preparation used in this study (Lot No. PBO 17011) was greater than 97% pure as determined by SDS-PAGE and had a ED50 of 0.05 to 0.2 ng/ml, measured as above.

Recombinant Murine Interleukin-13

Recombinant murine interleukin-13 (IL-13) was purchased from R & D Systems Inc. The preparation used in this study (lot no. 413-ML-025) was greater than 97% pure as determined by SDS-PAGE, and had an ED50 of 3 to 6 ng/ml.

Recombinant Murine Interleukin-15

Recombinant murine interleukin-15 (IL-15) was purchased from Protein Institute Inc. The preparation used in this study (lot no. P200-15) was greater than 98% pure as determined by SDS-PAGE and N-terminal sequence analysis. The preparation had an ED50 of less than 0.5 ng/ml, corresponding to a specific activity of $2 \times 10^6$ units/mg.

Recombinant Murine Interleukin-18

Murine interleukin-18 (IL-18) was purchased from Protein Institute Inc. The preparation used in this study (lot no. P 200-18) was greater than 98% pure as determined by SDS-PAGE and HPLC analysis. The preparation used in this study had an ED50 of 0.1 to 5 ng/ml.

Recombinant Murine Granulocyte-Macrophage Colony Stimulating Factor

Recombinant murine granulocyte-macrophage stimulating factor (GM-CSF) was purchased from Protein Institute Inc. The preparation used in this study (lot no. P 300 M-03) was greater than 98% pure as determined by SDS-PAGE and N-terminal sequence analysis. The preparation had an ED50 of 0.1 ng/ml.

Murine interferon α/β, recombinant murine IL-2, IL-4, IL-5, IL-I0, IL-12, IL-13, IL-1 5, IL-1 8, and GM-CSF were taken up in the Ferimmune™ excipient prior to administration.

Excipient

Cytokine preparations were diluted either in phosphate buffered saline (PBS) containing bovine serum albumin (BSA) or in the proprietary excipient described below. Bovine serum albumin fraction V (RIA grade; immunoglobulin free; Cat. No. A7888; Sigma, USA) was dissolved at a final concentration of 100 µg/ml in PBS (pH 7.4) and sterilized by filtration (0.2 µm, Millex-GV, Millipore, USA).

In most of the experiments described herein the cytokine preparations were diluted in a proprietary excipient. The excipient used was as follows, supplied in the form of tablets (Ferimmune™, Pharma Pacific):

|  | % w/w | mg/tablet |
|---|---|---|
| Dextrose (Glucose) BP** | 44.67*** | 55.84 |
| Gelatin BP** | 30.06 | 37.58 |
| Wheat Starch BP** | 11.31 | 14.14 |
| Carmellose Sodium BP** | 4.96 | 6.20 |
| Egg Albumin BPC** | 4.03 | 5.04 |
| Leucine USP | 3.00 | 3.75 |
| Propylene Glycol BP | 1.88 | 2.35 |
| Dextran 40** (as Dextran 40 Injection BP) | 0.06 | 0.08 |
| Sodium Phosphate BP | 0.03 | 0.04 |
| Sodium Chloride BP | 0.01 | 0.01 |
| Sodium Acid Phosphate BP | 0.01 | 0.01 |
| Total | 100.02 | 125.04 |

**calculated on an anhydrous basis
***derived from 44.64% of Dextrose (Glucose anhydrous) BP and 0.03% of Glucose BP (as Dextran 40 Injection BP)

A single Ferimmune™ excipient tablet (Lot No. B095002, expiry date September 1997) was dissolved in 1.5 ml of PBS in a 2 ml Eppendorf microfuge tube for three hours at room temperature on a rotary (end over end) mixer. The suspension was then centrifuged at 16,000 g for 15 minutes, and the supernatant was recovered. The Ferimmune™ excipient was prepared daily immediately prior to use.

II. Delivery System

Preliminary experiments showed that the application of 5 µl of crystal violet to each nostril of a normal adult mouse using a P20 Eppendorf micropipette resulted in an almost immediate distribution of the dye over the whole surface of the oropharyngeal cavity. Staining of the oropharyngeal cavity was still apparent some 30 minutes after application of the dye. This method of administration was therefore used in all subsequent experiments.

III. Experimental Materials
(1) EMCV (Encephalomyocarditis Virus)
    Batch: Lot No. 095001
    Expiration Date: December 1997
    Preparation: EMCV strain JH was propagated on mouse L929 cells using methods described in Gresser I, Bourali C, Thomas M T, Falcoff E. Effect of repeated inoculation of interferon preparations on infection of mice with encephalomyocarditis virus. Proc Soc Exp Biol Med 1968 February; 127:491-6.
    Characterization: The virus stock used in this study had a titer of 5×108.62TCID50 on mouse L929 cells.
(2) Friend Erythroleukaemia Cells
    The interferon-α/β-resistant clone, 3C18, of Friend erythroleukaemia cells (FLC) was obtained from Dr. E. Affabris, Rome and is described indetail by Affabris et al, 1982 (Virology, 120: 441–452). These cells were subsequently maintained by in vivo passage. Briefly, DBA/2 mice were inoculated by intraperitoneal injection (ip) with approximately 100 LD50 of 3C18 cells and one week later the tumor cells were harvested from the peritoneum of the mice, counted and other mice were again inoculated with 100 LD50 of 3C18 cells. This procedure was repeated for 60 to 100 passages. It has been shown that the 3C18 cells used at the 60th to 100th in vivo passage are highly metastatic for the liver and spleen (Gresser et al, Int. J. Cancer, 1987 39: 789–792). The phenotype of IFN resistance was confirmed routinely by cultivating the in vivo passaged cells in vitro in the presence of interferon-cc/p (Belardelli et al, Int. J. Cancer, 1982 30: 813–820).

IV. Experimental Animals

The mice used in this study were obtained from a specific pathogen-free colony (IFFA CREDO, France). They were housed in a specific pathogen-free animal facility at the Institut Federatif CNRS at Villejuif according to EEC standards.

EXAMPLE 1

Effect of Il-2 and IL-12 on Mice Challenged With a Lethal Dose of EMCV (Encephalomyocarditis virus)

Groups of ten, 6 week-old male Swiss mice were infected with 100 LD50 of Encephalomyocarditis Virus (EMCV). One hour after virus infection, mice were either left untreated, or treated once a day for 4 days by the intranasal/oral route with recombinant murine IL-2 or recombinant murine IL-12, in a volume of 10 µl of Ferimmune excipient or with 10 µl of excipient alone (control), or by intraperitoneal (IP) injection in 200 µl of excipient, or with 200 µl of excipient alone.

Treatment of adult mice with 2 µg of recombinant murine IL-2 per day for 4 days by the intranasal/oral route resulted in an increase in the percentage of animals surviving infection with a lethal dose of EMCV. Up to 40% of the animals treated were alive 100 days after infection with a lethal dose of EMCV, under conditions where all the untreated, or excipient treated virus-infected animals were dead at 6 days.

Treatment of adult mice with recombinant murine IL-2 by the intranasal/oral route resulted in a marked increase in the percentage of animals surviving infection with a lethal dose of EMCV. The increase in the percentage of animals surviving infection with a lethal dose of EMCV was dependent upon the dose of IL-2 administered by the intranasal/oral route. Thus, treatment of adult mice with 1 µl of recombinant murine IL-2 per day for 4 days by the intranasal/oral route resulted in the survival of 30% of animals infected with a lethal dose of EMCV, while treatment of animals with 3 µg of recombinant murine IL-2 per day for 4 days by the intranasal/oral route resulted in the survival of 60% of the animals. IL-2 treated animals were alive and well 100 days after infection with a lethal dose of EMCV, under conditions where all the untreated, or excipient treated virus-infected animals were dead at 6 days. In contrast, treatment of adult mice with 0.1 µg of recombinant murine IL-2 per day for 4 days by the intranasal/oral route did not increase significantly the survival of animals infected with a lethal dose of EMCV.

Animals treated with 0.1 or 1 µg of recombinant murine IL-2 per day for 4 days by the intranasal/oral route did not exhibit any detectable signs of toxicity. Signs of acute toxicity including shivering, lethargy, and ruffled fur, were observed, however, in animals treated by the intranasal/oral route with 3 µg of recombinant IL-2, the highest dose of IL-2 tested.

Treatment of adult Swiss mice with recombinant murine IL-12 by the intranasal/oral route was also found to increase the percentage of animals surviving infection with a lethal dose of EMCV, albeit to a lesser extent than with the same quantity of recombinant IL-2. Thus treatment of adult Swiss mice with 2 μg of recombinant murine IL-12 per day for 4 days by the intranasal/oral route, resulted in the 100 day survival of approximately 20% of the animals infected with a lethal dose of EMCV.

Clinical observations suggest that all the IL-2 treated and IL-12 treated animals alive at 100 days will survive.

Similarly, treatment of adult mice with recombinant murine IL-2 by the intraperitoneal route resulted in a dose dependent increase in the percentage of animals surviving infection with a lethal dose of EMCV. Thus, treatment of animals with 0.1 μg of recombinant murine IL-2 per day for 4 days by the intraperitoneal route did not increase significantly the survival of virus infected animals, while treatment of mice with 1 μg or 3 μg of recombinant murine IL-2 per day for 4 days by the intraperitoneal route resulted in the survival of 40% and 70% respectively of animals infected with a lethal dose of EMCV.

The results of the experiments presented herein suggest that the oromucosal route provides an effective means of administering very high doses of IL-2 with acceptable toxicity. Thus, animals treated with 0.1 or 1 μg of recombinant urine IL-2 per day for 4 days by the intranasal/oral route did not exhibit any detectable signs of toxicity. Based on body weight (0.025 kg for an adult mouse and a human adult body weight of 60 kg) this corresponds to an approximate human dose equivalent of 0.24 and 2.4 mg respectively or 24 and 240 times the maximum tolerated dose of parenterally administered IL-2 (Huland et al., 1994, *J Cancer Res. Clin. Oncol.* 120, 221–228).

The results of the experiments suggest that the oromucosal route provides an effective means of administering IL-2 and IL-12 without apparent toxicity. These results have important implications for the clinical use of IL-2 and IL-12 as antiviral agents.

EXAMPLE 2

Effect of IL-2 and IL-12 on Mice Challenged with Highly Metastatic Friend Leukemia Cells Groups of ten, 6 week old DBA/2 mice were challenged intravenously with 105 Friend leukemia cells (interferon resistant clone 3C18), equivalent to approximately 20,000 LD50 on day 0. Tumor-inoculated mice were either left; untreated, or treated twice a day for up to 20 days by the intranasal/oral route with recombinant murine IL-2 or recombinant murine IL-12, in a volume of 10 μl of Ferimmune excipient, or with 10 μl of excipient alone (control).

Treatment of adult mice with 2 μg of recombinant murine IL-2 twice a day for 20 days by the intranasal/oral route resulted in a marked increase in the survival time of animals inoculated with approximately 20,000 LD50 of Friend leukemia cells. Thus although none of the IL-2 treated, tumor inoculated animals survived for more than 32 days, treatment of adult DBA/2 mice with 2 μg of recombinant murine IL-2 twice a day for 20 days by the intranasal/oral route, resulted in a statistically significant increase in survival time (mean day of death, 22.6±2.08 days), relative to both untreated, or excipient-treated, tumor-inoculated animals (mean day of death, 13.8±0.13 days).

Treatment of adult DBAl2 mice with recombinant murine IL-12 by the intranasal/oral route was also found to increase the survival time of animals inoculated with a lethal dose of Friend leukemia cells, albeit to a lesser extent than with either the same quantity of recombinant IL-2. Thus although none of the IL-12 treated, tumor inoculated animals survived for more than 20 days, treatment of adult DBA/2 mice with 2 μg of recombinant murine IL-12 twice a day for up to 20 days by the intranasal/oral route, resulted in a statistically significant increase in survival time (mean day of death, 15.9±0.56 days), relative to both untreated, or excipient treated tumor inoculated animals (mean day of death, 13.8±0.13 days).

The results of the experiments show that recombinant murine IL-2 exhibits a marked antitumor activity in mice inoculated with highly metastatic Friend leukemia cells, following administration by the intranasal/oral route. These results are remarkable as recombinant IL-2 administered systemically has previously been reported to be completely ineffective in increasing the survival time of mice inoculated intravenously with Friend leukemia cells (Belardelli et al., 1989, Int. J. Cancer, 44:1108–116). The results also suggest that the oromucosal route provides an effective means of administering IL-2 without apparent toxicity.

EXAMPLE 3

Effect of Combined IL-2 and IFN on Mice Challenged with a Lethal Dose of EMCV

Groups of ten, 6 week-old male Swiss mice were infected with 100 LD50 of EMCV. One hour after virus infection, mice were either left untreated, or treated once a day for 4 days by either the intranasal/oral or intraperitoneal routes with 1.0 μg of recombinant murine IL-2, $10^3$ IU of murine interferon α/β, or the same dose of recombinant murine IL-2 and murine interferon α/β, in the Ferimmune™ excipient, or with an equal volume of excipient along (control). Alternatively, mice were treated by intraperitoneal injection with the same dose of recombinant murine IL-2, murine interferon α/β, or recombinant murine IL-2 and murine interferon α/β.

In order to determine whether administration of recombinant murine IL-2, together with murine interferon α/β would result in an additive or even synergistic antiviral effect, animals were treated initially by the intranasal/oral route with recombinant murine IL-2, followed 30 minutes later with murine interferon α/β. Treatment of adult mice with recombinant murine IL-2 together with murine interferon α/β by the intranasal/oral route resulted in an additive increase in the percentage of animals surviving infection with a lethal dose of EMCV. Thus, treatment of adult mice once a day for 4 days by the intranasal/oral route with 1 μg of recombinant murine IL-2 followed by $10^3$ IU of murine interferon α/β resulted in the survival of 80% of the animals infected with a lethal dose of EMCV.

Treatment of adult mice with 1.0 μg of recombinant murine IL-2 followed 30 minutes later with $10^3$ IU of murine interferon α/β by the intraperitoneal route resulted in the survival of 80% of the animals infected with a lethal dose of EMCV.

Animals treated once a day for 4 days with 1 μg of recombinant murine IL-2, $10^3$ IU of interferon α/β, or both recombinant murine IL-2, and interferon α/β, either by the intranasal/oral or intraperitoneal routes did not exhibit any detectable signs of toxicity.

EXAMPLE 4

Effect of Various Th1 and Th2 Cytokines on Mice Challenged with a Lethal Dose of EMCV Groups of ten, 6 week-old male Swiss mice were infected with 100 LD50 of EMCV. Following virus infection, mice were either left untreated, or treated once a day for 4 days by the intranasal/oral route with murine IFN α/β, recombinant murine IL-2, IL-4, IL-10, IL-12, or IL-15 in a volume of 10 μl of Ferimmune excipient, or with 10 μl of excipient alone (control).

Treatment of adult mice with murine interferon α/β by the intranasal/oral route resulted in a marked increase in the percentage of animals surviving infection with a lethal dose of EMCV. Thus, 50% of the animals treated with $10^3$ IU of murine interferon α/β were alive 86 days after infection with a lethal dose of EMCV, under conditions where all the untreated, or excipient treated virus-infected animals were dead at 7 days. Treatment of adult mice with 1 μl of recombinant murine IL-2 per day for 4 days by the intranasal/oral route also resulted in a marked increase in the percentage of animals surviving infection with a lethal dose of EMCV. Thus, 30% of the animals treated with recombinant murine IL-2 by the intranasal/oral route were alive 86 days after virus infection. Similarly, treatment of adult mice with 1 μg of recombinant murine IL-15 per day for 4 days by the intranasal/oral route also resulted in the survival of 30% of animals infected with a lethal dose of EMCV. Treatment of adult mice with 1 μg of recombinant murine GM-CSF per day for 4 days by the intranasal/oral route also resulted in the survival of 20% of animals infected with a lethal dose of EMCV.

Treatment of adult Swiss mice with recombinant murine IL-12 by the intranasal/oral route was also found to increase the percentage of animals surviving infection with a lethal dose of EMCV, albeit to a lesser extent than with either the same quantity of recombinant IL-2 or IL-15. Thus, treatment of adult Swiss mice with 1 μg of recombinant murine IL-12 per day for 4 days by the intranasal/oral route, resulted in the survival of approximately 20% of the animals infected with a lethal dose of EMCV.

Clinical observations suggest that all the interferon-treated, IL-2 treated, IL-12 treated, and IL-15 treated and GM-CSF treated animals alive at 86 days will survive for a normal life span.

In contrast, treatment of animals with 1 μg of recombinant murine IL-4 or IL-10 per day for 4 days by the intranasal/oral route, did not result in a significant increase in the survival of animals infected with a lethal dose of EMCV. Thus, all the IL-4 and IL-10 treated mice were dead 8 days after virus infection, that is within 24 hours of the untreated, or excipient treated virus-infected animals.

EXAMPLE 5

Effect of Various Th1 and Th2 Cytokines on Mice Challenged with a Lethal Dose of EMCV Groups of ten, 6 week-old Swiss mice were infected with 100 LD50 of EMCV. Following virus infection, mice were either left untreated, or treated once a day for 4 days by the intranasal/oral route with murine IFN α/β, recombinant murine IL-5, IL-13, or IL-18, in a volume of 10 μl of Ferimmune excipient, or with 10 μl of excipient alone (control).

Treatment of adult mice with murine interferon α/β by the intranasal/oral route resulted in a marked increase in the percentage of animals surviving infection with a lethal dose of EMCV. Thus, 50% of the animals treated with $10^3$ IU of murine interferon α/β were alive 52 days after infection with a lethal dose of EMCV, under conditions where all the untreated, or excipient treated virus-infected animals were dead at 6 days. Treatment of adult mice with 1 μg of recombinant murine IL-18 per day for 4 days by the intranasal/oral route also resulted in a marked increase in the percentage of animals surviving infection with a lethal dose of EMCV. Thus, 20% of the animals treated with recombinant murine IL-18 by the intranasal/oral route were alive 52 days after virus infection.

Clinical observations suggest that all the interferon-treated and the IL-18 treated animals alive at 52 days will survive for a normal life span.

In contrast, treatment of animals with 1 μg of recombinant murine IL-5, or IL-13 per day for 4 days by the intranasal/oral route, did not result in a significant increase in the survival of animals infected with a lethal dose of EMCV. Thus, all the IL-5 and IL-13 treated mice were dead 9 days after virus infection, that is within 72 hours of the untreated or excipient treated virus-infected animals.

None of the animals treated with 1,000 IU of IFN α/β, or 1 μg of recombinant murine IL-5, IL-13, or IL-18 per day for 4 days by the intranasal/oral route, exhibited detectable signs of toxicity suggesting that the oromucosal route provides an effective means of administering cytokines, in the absence of apparent toxicity.

IL-4 and IL-10, which are both potent stimulators of Th2 reactivity, were found to be devoid of antiviral activity following administration by the intranasal/oral route, emphasizing the close association between the ability to induce Th1 reactivity and the induction of antiviral activity following oromucosal administration.

EXAMPLE 6

Effect of IFN on Mice Challenged with Ragweed Pollen

The preparation of interferon α/β used in this study (lot no. RT6) had a titer of $1 \times 10^7$ IU/ml and a specific activity of $5 \times 10^7$ IU/mg protein as assayed on mouse L929 cells challenged with Vesicular Stomatitis virus (VSV). (Tovey et al, Proc. Soc. Exp. Biol. Med., 1974, 146:406–415).

Murine IFN α/β was taken up in the bovine serum alburnin/phosphate buffered saline (BSA/PBS) excipient prior to administration.

Groups of four, 8 week old male Swiss or Balb/c mice were immunized by intraperitoneal injection on days 0 and 4 with 200 μg of non-defatted pyrogen-free ragweed pollen allergen (Greer Laboratories, Lenoir, USA) in alum adjuvant (Imject Alum, Pierce Laboratories). Mice were then challenged by the intratracheal route with 200 μg of ragweed allergen in Coca's buffer (0.085 M NaCl 0.064 M NaHCO$_3$, pH 8.1) on day 11. Groups of animals were treated by the oromucosal route with either 1000 IU of murine IFN α/β in a volume of 10 μl of excipient or with 10 μl of excipient alone (Tovey et al, Proc. Soc. Exp. Biol. Med., 1974, 146:406–415) once a day from days 0 to 6 inclusive. Other groups of animals were treated intraperitoneally with either $10^3$ IU of murine IFN α/β in a volume of 200 μl of excipient or with 200 μl of excipient alone (control) once a day from days 0 to 6 inclusive. Groups of animals were also treated by the oromucosal or intraperitoneal routes with either 1000 IU of murine IFN α/β in a volume of 10 μl or 200 μl of excipient respectively, or with 10 μl or 200 μl of excipient alone (control) twice on day 11 and once on day 12 only. Further groups of animals were treated as above on days 0 to 6 and 11 to 12. All animals were sacrificed on day 14 and samples of peripheral blood, and bronchoalveolar washing (BAL) were harvested.

Samples of peripheral blood were collected in vacuum tubes containing EDTA (B.D., catalogue no 367624), centrifuged at 800×g for 10 minutes at 4° C., the serum was collected and analyzed for the presence of IgG or IgE ragweed pollen specific antibody using an Enzyme Linked Immunoabsorption Assay (ELISA).

Briefly, serum samples were pre-diluted 1:100 in PBS and further serially diluted in microtiter plates (Maxisorb, Nunc) coated with ragweed pollen (20 µg/ml) in 0.1 M $NaHCO_3$, pH 8.5. Ragweed specific IgG or IgE was detected using alkaline phosphatase labelled goat, anti-mouse IgG or a biotin-conjugated rat monoclonal anti-mouse IgE followed by alkaline phosphatase-conjugated streptavidine respectively. Mean absorbance (405 nm) was determined using duplicate samples.

Immunization of 8 week old male Balb/c mice with pyrogen-free ragweed pollen allergen by intraperitoneal injection on days 0 and 4 followed by intratracheal challenge on day 11, resulted in high levels of IgG and IgE ragweed pollen specific antibody determined at 14 days.

Treatment of animals by the oromucosal route with 1000 IU of murine IFN α/β once a day from days 0 to 6 inclusive and on days 11 to 12 resulted in a marked inhibition of IgE allergen specific antibody production relative to animals treated with mock interferon. Oromucosal interferon treatment also inhibited the allergen specific IgG antibody response albeit to a lesser extent than the IgE response. Treatment of animals by the oromucosal route with 1000 IU of murine IFN α/β on either days 0 to 6 only, or on days 11 to 12 only, resulted in a less marked inhibition of antibody production than combined treatment.

Treatment of animals by the oromucosal route with 1000 IU of murine IFN α/β once a day from days 0 to 6 inclusive and on days 11 to 12, or on days 11 and 12 only, resulted in a greater inhibition of IgE allergen specific antibody production than in animals injected intraperitoneally with 1000 IU of murine IFN α/β.

Treatment of animals by the oromucosal route with 1000 IU of murine IFN α/β once a day from days 0 to 6 inclusive and on days 11 to 12 resulted in three-fold inhibition in the number of eosinophils present in peripheral blood relative to animals treated with mock interferon. Treatment of animals by the oromucosal route with 1000 IU of murine IFN α/β resulted in a two-fold more marked inhibition of eosinophil numbers than in animals injected intraperitoneally with 1000 IU of murine IFN α/β. Treatment of animals by the oromucosal or intraperitoneal routes with 1000 IU of murine IFN α/β on days 11 and 12 only, did not result in any detectable inhibition of the number of circulating eosinophils present in peripheral blood and in the case of oromucosal interferon treatment may even have caused a slight increase in the percentage of eosinophils relative to animals treated with mock interferon.

The effect of oromucosal IFN α therapy on the allergen specific IgE response and allergen-induced eosinophil recruitment appeared to be less marked than that previously reported for IL-12 tested in the same animal model of allergen induced atopic asthma (Sur et al., J. Immunol. 1996, 157, 4173–4180). It is probable, however, that correspondingly greater effects will be observed at higher doses of IFN than the relatively low single dose of 1000 IU employed in the studies described herein, which on a weight basis is 200 fold lower than the dose of IL-12 used by Sur et al. Although IL-12 is one of the most effective cytokines tested in animal models of allergen induced atopic asthma when therapy is initiated early during the period of allergic sensitization, IL-12 is totally ineffective, however, in reducing the allergen specific IgE response when therapy is initiated late in the development of the disease process during the period of the hypersensitive inflammatory response in the lungs. In contrast, oromucosal interferon alpha therapy appeared to be effective in reducing the allergen specific IgE response even when therapy was initiated late in the development of the disease.

The results of the studies reported herein show that oromucosal IFN α therapy markedly reduced both the allergen specific IgE response and allergen-induced eosinophil recruitment in animals sensitised to the common human allergen ragweed pollen. The effect of oromucosal interferon therapy on two of the hallmarks of atopic asthma suggest that oromucosal IFN α therapy may find application in the treatment of asthma, although caution should be exercised when extrapolating from a rodent model to a clinical setting, even when using a common human allergen.

The demonstration that Th1 specific cytokines exhibit marked activity following administration by the oromucosal route indicates that the oromucosal administration of cytokines can be used to induce systemic Th1 reactivity, which is known to play an important role in host defense against virus infection and neoplastic disease.

The oromucosal administration of biologically active but poorly tolerated Th1 cytokines is of considerable potential importance for the treatment of both viral and neoplastic diseases. Oromucosal administration of Th1 cytokines may also find application in the treatment of diseases such as asthma and atopic dermatitis. Oromucosal administration of Th2 cytokines has been shown to be ineffective in treating the cancer and viral conditions responsive to oromucosal Th1 cytokines. This observation is consistent with the known roles of Th1 and Th2 in the host defense mechanism. Conditions expected to be responsive to Th2 cytokines are then those characterized by Th1 overstimulation, such as autoimmune diseases. Oromucosal administration of a Th2 cytokine may find application in the treatment of rheumatoid arthritis, Type I diabetes, lupus, multiple sclerosis, and psoriasis.

I claim:

1. A method for treating diseases that would benefit from TH1 stimulation, comprising stimulating the host defense mechanisms in a mammal having such a disease by oromucosally administering an effective amount of a TH1-stimulating cytokine selected from the group consisting of IL-12, IL-18, TNF-β and GM-CSF, wherein said oromucosal administration is accomplished in a manner that provides contact of the cytokine with the oromucosal cavity of the recipient for a period of time sufficient to obtain the desired stimulation.

2. A method in accordance with claim 1, wherein said disease that would benefit from TH1 stimulation is selected from the group consisting of neoplastic conditions, viral conditions, allergic disorders, asthma and atopic dermatitis.

3. A method in accordance with claim 1, wherein said effective amount is large enough to generate a pathological response if said cytokine were administered parenterally in that amount.

4. A method in accordance with claim 2, wherein said disease is selected from the group consisting of neoplastic conditions and viral conditions.

5. A method in accordance with claim 4, wherein said disease is a viral condition.

6. A method in accordance with claim 4, wherein said disease is a neoplastic condition.

7. A method of claim 6, wherein the effective amount of cytokine is from about 0.01 µg to about 150 µg of cytokine per kg body weight.

8. A method of claim 6, in which the effective amount of cytokine is administered in a single amount.

9. A method of claim 6, in which the effective amount of cytokine is administered in a plurality of amounts, each smaller than the effective amount, over a period of time sufficient to elicit stimulation equivalent to that of a single effective amount.

10. A method of claim 6, in which the effective amount of cytokine is administered continuously over a period of time sufficient to elicit stimulation equivalent to that of a single effective amount.

11. A method in accordance with claim 2, wherein said disease is selected from the group consisting of allergic disorders, asthma, and atopic dermatitis.

12. A method of claim 11, wherein the effective amount of cytokine is from about 0.01 µg to about 150 µg of cytokine per kg body weight.

13. A method of claim 11, in which the effective amount of cytokine is administered in a single amount.

14. A method of claim 11, in which the effective amount of cytokine is administered in a plurality of amounts, each smaller than the effective amount, over a period of time sufficient to elicit stimulation equivalent to that of a single effective amount.

15. A method of claim 11, in which the effective amount of cytokine is administered continuously over a period of time sufficient to elicit stimulation equivalent to that of a single effective amount.

16. A method in accordance with claim 11, wherein said disease is an allergic disorder.

17. A method in accordance with claim 11, wherein said disease is asthma.

18. A method in accordance with claim 11, wherein said disease is atopic dermatitis.

19. A method for treating diseases that would benefit from TH1 stimulation, comprising stimulating the host defense mechanisms in a mammal having such a disease by oromucosally administering, in a single dose, an effective amount of a TH1-stimulating cytokine selected from the group consisting of IL-2, IL-12, IL-15, IL-18, TNF-β and GM-CSF, wherein said oromucosal administration is accomplished in a manner that provides contact of the cytokine with the oromucosal cavity of the recipient for a period of time sufficient to obtain the desired stimulation.

20. A method in accordance with claim 19, wherein said disease that would benefit from TH1 stimulation is selected from the group consisting of neoplastic conditions, viral conditions, allergic disorders, asthma and atopic dermatitis.

21. A method in accordance with claim 20, wherein said disease is selected from the group consisting of neoplastic conditions and viral conditions.

22. A method in accordance with claim 21, wherein said disease is a neoplastic condition.

23. A method of claim 19, wherein the effective amount of cytokine is from about 0.01 µg to about 150 µg of cytokine per kg body weight.

24. A method in accordance with claim 21, wherein said disease is a viral condition.

25. A method in accordance with claim 20, wherein said disease is selected from the group consisting of allergic disorders, asthma, and atopic dermatitis.

26. A method in accordance with claim 25, wherein said disease is an allergic disorder.

27. A method in accordance with claim 25, wherein said disease is asthma.

28. A method in accordance with claim 25, wherein said disease is atopic dermatitis.

29. A method of claim 25, wherein the effective amount of cytokine is from about 0.01 µg to about 150 µg of cytokine per kg body weight.

30. A method in accordance with claim 19, wherein said effective amount is large enough to generate a pathological response if said cytokine were administered parenterally in that amount.

31. A method for treating allergic disorders, asthma or atopic dermatitis, comprising stimulating the host defense mechanisms in a mammal having such a disease by oromucosally administering an effective amount of a TH1-stimulating cytokine selected from the group consisting of IL-2, IL-12, IL-15, IL-18, TNF-β and GM-CSF, wherein said oromucosal administration is accomplished in a manner that provides contact of the cytokine with the oromucosal cavity of the recipient for a period of time sufficient to obtain the desired stimulation.

32. A method of claim 31, wherein the effective amount of cytokine is from about 0.01 µg to about 150 µg of cytokine per kg body weight.

33. A method of claim 31, in which the effective amount of cytokine is administered in a single amount.

34. A method of claim 31, in which the effective amount of cytokine is administered in a plurality of amounts, each smaller than the effective amount, over a period of time sufficient to elicit stimulation equivalent to that of a single effective amount.

35. A method of claim 31, in which the effective amount of cytokine is administered continuously over a period of time sufficient to elicit stimulation equivalent to that of a single effective amount.

36. A method in accordance with claim 31, wherein said disease is an allergic disorder.

37. A method in accordance with claim 31, wherein said disease is asthma.

38. A method in accordance with claim 31, wherein said disease is atopic dermatitis.

39. A method in accordance with claim 31, wherein said effective amount is large enough to generate a pathological response if said cytokine were administered parenterally in that amount.

40. A method for treating diseases that would benefit from TH1 stimulation, comprising stimulating the host defense mechanisms in a mammal having such a disease by oromucosally administering IL-2 or IL-15 in an effective amount that is great enough to generate a pathological response if administered parenterally, wherein said oromucosal administration is accomplished in a manner that provides contact of the cytokine with the oromucosal cavity of the recipient for a period of time sufficient to obtain the desired stimulation.

41. A method in accordance with claim 40, wherein said disease that would benefit from TH1 stimulation is selected from the group consisting of neoplastic conditions, viral conditions, allergic disorders, asthma and atopic dermatitis.

42. A method in accordance with claim 41, wherein said disease is selected from the group consisting of neoplastic conditions and viral conditions.

43. A method in accordance with claim 42, wherein said disease is a neoplastic condition.

44. A method of claim 43, in which the effective amount of cytokine is administered in a single amount.

45. A method of claim 43, in which the effective amount of cytokine is administered in a plurality of amounts, each smaller than the effective amount, over a period of time sufficient to elicit stimulation equivalent to that of a single effective amount.

46. A method of claim 43, in which the effective amount of cytokine is administered continuously over a period of time sufficient to elicit stimulation equivalent to that of a single effective amount.

47. A method in accordance with claim 42, wherein said disease is a viral condition.

48. A method in accordance with claim 41, wherein said disease is selected from the group consisting of allergic disorders, asthma, and atopic dermatitis.

49. A method in accordance with claim 48, wherein said disease is an allergic disorder.

50. A method in accordance with claim 48, wherein said disease is asthma.

51. A method in accordance with claim 48, wherein said disease is atopic dermatitis.

52. A method of claim 48, in which the effective amount of cytokine is administered in a single amount.

53. A method of claim 48, in which the effective amount of cytokine is administered in a plurality of amounts, each smaller than the effective amount, over a period of time sufficient to elicit stimulation equivalent to that of a single effective amount.

54. A method of claim 48, in which the effective amount of cytokine is administered continuously over a period of time sufficient to elicit stimulation equivalent to that of a single effective amount.

55. A method for treating diseases that would benefit from TH2 stimulation, comprising stimulating the host defense mechanisms in a patient having such a disease by oromucosally administering an effective amount of a TH2-stimulating cytokine selected from the group consisting of IL-4, IL-5 and IL-13, wherein said oromucosal administration is accomplished in a manner that provides contact of the cytokine with the oromucosal cavity of the recipient for a period of time sufficient to obtain the desired stimulation.

56. A method in accordance with claim 55, wherein said disease that would benefit from TH2 stimulation is an autoimmune disease.

57. A method of claim 56, in which the effective amount of cytokine is from about 0.01 µg to about 150 µg of cytokine per kg body weight.

58. A method of claim 56, in which the effective amount of cytokine is administered in a single amount.

59. A method of claim 56, in which the effective amount of cytokine is administered in a plurality of amounts, smaller than the effective amount, over a period of time sufficient to elicit stimulation equivalent to that of a single effective amount.

60. A method of claim 56, in which the effective amount of cytokine is administered continuously over a period of time sufficient to elicit stimulation equivalent to that of a single effective amount.

61. A method in accordance with claim 55, wherein said effective amount is large enough to generate a pathological response if said cytokine were administered parenterally in that amount.

62. A method for treating diseases that would benefit from TH2 stimulation, comprising stimulating the host defense mechanism in a patient having such a disease by oromucosally administering IL-10 in an effective amount that is great enough to generate a pathological response if administered parenterally, wherein said oromucosal administration is accomplished in a manner that provides contact of the cytokine with the oromucosal cavity of the recipient for a period of time sufficient to obtain the desired stimulation.

63. A method in accordance with claim 62, wherein said disease that would benefit from TH2 stimulation is an autoimmune disease.

64. A method of claim 63, in which the effective amount of cytokine is administered in a single amount.

65. A method of claim 63, in which the effective amount of cytokine is administered in a plurality of amounts, smaller than the effective amount, over a period of time sufficient to elicit stimulation equivalent to that of a single effective amount.

66. A method of claim 63, in which the effective amount of cytokineis administered continuously over a period of time sufficient to elicit stimulation equivalent to that of a single effective amount.

* * * * *